United States Patent [19]
Smuckler

[11] Patent Number: 5,124,076
[45] Date of Patent: Jun. 23, 1992

[54] RAPID, CURING, ELECTRICALLY CONDUCTIVE ADHESIVE

[75] Inventor: Jack H. Smuckler, Marblehead, Mass.

[73] Assignee: Contour Electrodes, Inc., Herrin, Ill.

[21] Appl. No.: 467,743

[22] Filed: Jan. 19, 1990

[51] Int. Cl.$^5$ .............................................. H01B 1/06
[52] U.S. Cl. ................... 252/518; 252/500; 128/640
[58] Field of Search ............... 252/500, 518; 128/640, 128/303.13, 798, 799, 803

[56] References Cited

U.S. PATENT DOCUMENTS

| | | | |
|---|---|---|---|
| 4,273,135 | 6/1981 | Larimore et al. | 128/640 |
| 4,352,359 | 10/1982 | Larimore et al. | 128/640 |
| 4,391,278 | 7/1983 | Cahalan et al. | 128/640 |
| 4,515,162 | 5/1985 | Yamamoto et al. | 128/640 |
| 4,524,087 | 6/1985 | Engel | 427/2 |
| 4,539,996 | 9/1985 | Engel | 128/640 |
| 4,554,924 | 11/1985 | Engel | 128/640 |
| 4,593,053 | 3/1986 | Jevne | 523/111 |
| 4,699,146 | 10/1987 | Sieverding | 128/640 |
| 4,750,482 | 6/1988 | Sieverding | |
| 4,777,954 | 10/1988 | Keush et al. | |

FOREIGN PATENT DOCUMENTS 168917 1/1986 European Pat. Off.
322098 6/1989 European Pat. Off.

Primary Examiner—Josephine Barr
Attorney, Agent, or Firm—Testa, Hurwitz & Thibeault

[57] ABSTRACT

Adhesive precursor compositions comprising an N-vinyl lactam monomer and an acrylic monomer mixed together in a ratio of between 10:1 to 1:10 can be polymerized rapidly and efficiently in situ in less than 30 seconds, and preferably less than 10 seconds, upon exposure to UV light. The electrically conductive hydrogel compositions consist essentially of the polymerizable monomers, water, a cross-linking agent, an ionizable salt, and a photoinitiator.

7 Claims, 1 Drawing Sheet

RAPID, CURING, ELECTRICALLY CONDUCTIVE ADHESIVE

BACKGROUND OF THE INVENTION

The present invention relates to a rapidly polymerizing, ionic, conformable, electrically conductive adhesive for use in disposable biomedical electrodes, and to a method for production of such electrodes. More particularly, this invention relates to an electrically conductive, adhesive hydrogel that does not require the addition of a humectant or plasticizer, and that can polymerize in less than 30 seconds to produce an essentially dry conductive adhesive that is easily removed. The adhesive may also be used as a nonconductive biomedical adhesive in, for example, occlusive bandages, ostomy gaskets, and drug delivery systems.

The need for conductive adhesives useful in biomedical electrodes is well-documented in the art. To have utility, the adhesive should have good electrical conductivity, conform well to the skin surface, and be sufficiently adhesive to maintain a stable connection with the skin surface, yet be cohesive enough to pull away readily from the skin without leaving a residue when the electrode is removed. In addition, the electrode should be easy to manufacture, and easy to package.

Conductive adhesives used in currently available biomedical electrodes are generally "dry" gel adhesives composed primarily of a crosslinked synthetic polymer or interpolymer matrix. The gel is formed by dispersing a polymer or polymer mix in a solvent, applying the viscous liquid to the surface where adhesive properties are desired, and then crosslinking the polymers by exposing them to ionizing radiation, (X-ray, gamma, or electron beam radiation), or to heat. Alternatively, a crosslinking agent may be added to the solution and crosslinking may be induced by means of a chemical catalyst or by a photoinitiator and UV light. The act of crosslinking will absorb a certain amount of liquid, and as long as the initial liquid content is not too great, the crosslinked product formed is a "dry"gel or film. In some cases, especially if the solvent is aqueous, it may be necessary to let the crosslinked matrix stand overnight in air, or under nitrogen, to evaporate unbound water.

Appropriate combinations of interpolymers also have the effect of forming a solid matrix, although because they are not crosslinked they cannot absorb as much liquid. Gum karaya, a swellable, naturally-occuring ionic polymer base, has also been used as a matrix. However, the inability to control its chemical and physical properties, and the gum's potential for stimulating adverse skin reactions and microbial growth have limited its utility.

The gel adhesives of the art typically also comprise water and a polyhydric alcohol in addition to the polymer. Water provides excellent electrical conductivity properties. However, the optimum water content for electrical conductivity is often compromised in an effort to achieve better adhesion and cohesion. Polyhydric alcohols such as polyethylene glycol are generally added in substantial amounts (30-50%) as humectants or plasticizers to increase the conformability of the adhesive. A humectant is especially important when gels are formed substantially of homopolymers, as these gels tend to be brittle. Such concentrations of polyhydric alcohols can be irritating to the skin.

Ionizing salts are generally added to provide electrical conductivity, although in some cases water-soluble polymers or ionic polymers are relied on to provide conductivity. In this case, a neutralizing base may be added to promote the ionic properties of, for example, acrylic acid.

Other additives, particularly tackifiers, also may be added to the composition. However, tackifiers have not been found particularly helpful in optimizing the electrical adhesive properties of such compositions. In addition, prolonged storage tends to diminish the tack in these compositions, possibly as a result of esterification crosslinking of the tackifier.

The gel adhesives of the art contain a number of deficiencies, among them, the requirement for a polyhydric alcohol, a maximum aqueous volume that is lower than the optimum level for electrical conductivity, and an inefficient and costly synthesis process.

U.S. Pat. Nos. 4,699,146; 4,750,482; and 4,772,954 all claim compositions of polymers that are cross-linked in situ by exposure to high energy radiation (approximately 0.25-5.0 millirads). The '146 and '482 patents, (both to Sieverding), disclose a matrix of polyvinylpyrrolidone, polyethylene glycol and water. The '954 patent (Keusch et al.), discloses a polyethylene oxide-water matrix that may contain an ionizing salt.

In addition to being expensive and posing severe space constraints, high energy radiation can produce undesired reactive species. This makes use of the process difficult to control and makes the effect of additional constituents difficult to predict.

U.S. Pat. No. 4,593,053 (Jevne et al.) discloses a hydrogel comprising polyvinylpyrrolidone, water, a polyvinyl alcohol, a polyhydric alcohol humectant, and salt. The composition is first heated to 130° C. to crosslink the polymer, then applied to the desired surface and allowed to cool in air to a non-liquid state.

EPO 168,917 discloses a polyacrylamide-disaccharide composition that includes a crosslinking agent and water, and which polymerizes in air in 30 minutes in the presence of a chemical catalyst.

U.S. Pat. Nos. 4,352,359 and 4,273,135 (both to Larimore et al.) disclose compositions of interpolymers and plasticizers. The adhesives may also include tackifiers. The interpolymers are not crosslinked, which limits the amount of solution or polar humectant the matrix can absorb. The compositions are knife-coated onto the electrode and allowed to air dry overnight.

U.S. Pat. No. 4,391,278 (Cahalan et al.) discloses a composition comprising 2-acrylamido-2-methopropanesulfonic acid, a humectant, water and a tackifier. Crosslinking occurs under nitrogen in five minutes in the presence of a chemical initiator.

The time and/or space constraint imposed by the cross-linking or "curing" step in each of the above patents limits their utility when the mass production of the compositions is considered. Compositions that require nitrogen chambers or high radiation sources for polymerization would require substantial increased expenses in equipment, production space and power. Adhesives that require substantial polymerization or drying time would require the allocation of too much valuable production space to render their mass production cost-efficient.

Recently, another method of gel adhesive formation has been developed. The method involves forming a precursor solution of monomers and other desired components, applying this viscous precursor to the electrode and allowing polymerization and crosslinking of the monomers to occur together. This method allows the absorption of a larger volume of the solvent. Typically the solvents are aqueous and the adhesives are referred to as hydrogels. The ability to absorb larger aqueous volumes allows one to take advantage of the superior conductive properties of water. However, the choice of monomers in the hydrogels has limited the amount of water the matrix can absorb without losing tack and cohesion. Moreover, the preferred hydrogels of the art still incorporate substantial amounts of humectants or plasticizers for conformability U.S. Pat. Nos. 4,524,087, 4,554,924, 4,539,996 and 4,848,353 (all to Engel) disclose monomeric adhesive precursor compositions that are polymerized in situ in the presence of a crosslinking agent, a photoinitiator, and UV light.

The '087 and '996 Engel patents require at least one ionic monomer, a polyhydric alcohol, a crosslinker, water, a neutralizing base, and an initiator. The ionic monomers listed are salts of unsaturated carboxylic acids. The '924 patent discloses a similar composition but comprising nonionic monomers instead of ionic monomers, and does not require a neutralizing base. An aqueous solution comprising an ionizing salt provides electrical conductivity. The nonionic monomer is acrylic acid or N-vinyl pyrrolidone, and in all examples discloses a tackifier to provide sufficient tack.

The '353 patent discloses a copolymer matrix of hydrogen bond donating monomers and hydrogen bond accepting monomers (a carboxylic acid and N-vinyl pyrrolidone, respectively). The monomers are present in a particular ratio (1:2 to 3:1, acid to pyrrolidone), and the hydrogen bond donating sites must be between about 5% to 80% neutralized (by addition of a neutralizing base such as sodium hydroxide, for example). Increasing the concentration of the vinyl pyrrolidone under these conditions yields soft hydrogels that leave a residue on the skin upon removal (EPO 322,098). Covalent cross-linking and humectants are purportedly not required, although a crosslinking agent is included in all examples described, and all preferred electrode adhesives contain about 50% glycerol The Engel hydrogels (0.1–0.8 mm thick) all require one to four minutes of curing in a three-foot inert nitrogen atmosphere chamber under a bank of 30 18" "black light" UV tubes. The maximum "curing" production rate would thus be about 180 feet per hour. In addition, nitrogen chambers are expensive. Although the production rate could be increased by using a larger chamber, it would require an increased expense in equipment, allocation of production space for the larger chamber, and the added cost of powering the large bank of UV lamps and larger supply of nitrogen. Eliminating the nitrogen chamber would require longer curing times and/or a greater intensity of UV light, as UV radiation is less efficient in air.

U.S. Pat. No. 4,842,768 (Nakao, et al.) claims a hydrogel adhesive formed of an ionic monomer, two different alkyl methacrylates, a polyhydric alcohol, a photoinitiator, and water. The composition is polymerized under nitrogen by exposure to UV light from "two parallely disposed 30 W" chemical lamps for five minutes.

EPO 322,098 (Duan) discloses hydrogel adhesives comprised of one monomeric species (N-vinyl pyrrolidone), water, a polyhydric alcohol, a photoinitiator and a particular class of crosslinking agents (multiethylenically unsaturated compounds containing vinyl, allyl or methallyl groups bonded to nitrogen or oxygen atoms). The use of N-vinylpyrrolidone as the primary polymer precursor allows the composition to absorb polar liquids. However, a humectant is still required in these compositions. Curing is said to occur within 0.5 minutes to 5 hours "depending on the intensity of the radiation and the opacity of the adhesive." Optimum conditions for curing a 0.89 mm thick gel appear to require curing at a distance of approximately 1 foot and curing times on the order of 10 to 15 minutes. Decreasing the curing distance between the adhesive and the UV source to about 6 inches would reduce curing times to about five minutes.

None of the adhesives of the art succeed at providing all the requirements for a cohesive, conformable biomedical adhesive that can be efficiently produced and does not require substantial quantities of a humectant. Accordingly, it is an object of this invention to provide a hydrogel for use as a biomedical adhesive that has superior adhesive and cohesive properties and that can be produced efficiently. Other objects are to provide a hydrogel adhesive that does not require a humectant; to provide an adhesive with superior conductive properties without compromising the requirement for adhesion and cohesion; and to provide a hydrogel adhesive that is capable of being cured rapidly and efficiently, e.g, in substantially less than 30 seconds when exposed to light from a UV lamp providing 200 Watts per linear inch intensity.

Another object is to provide a method for producing a rapidly polymerizing adhesive.

These and other objects and features of the invention will be apparent from the description, drawing, and claims that follow.

SUMMARY OF THE INVENTION

It has now been discovered that adhesive precursor compositions comprising an N-vinyl lactam monomer and an acrylic monomer mixed together in a ratio of between 10:1 to 1:10 can be polymerized rapidly and efficiently in a cavity of a biomedical electrode. More specifically, compositions of the invention can be polymerized in situ in less than 30 seconds, and preferably in less than 10 seconds, upon exposure to UV light providing an intensity of 200 W per linear inch. The electrically conductive hydrogel composition consists essentially of the polymerizable monomers, water, a crosslinking agent, an ionizable salt, and a photoinitiator. It is cohesive, adhesive, conformable, and sufficiently elastic without the presence of a humectant or plasticizer.

As a result of these discoveries a new hydrogel adhesive has been developed, as well as a method for its efficient production. The method includes assembling a precursor comprising an aqueous solution of N-vinyl lactam monomer and acrylic monomer, wherein the monomers are present in a ratio of between 1:10 to 10:1. The precursor is then placed in a well defined by a UV-translucent, adhesive (non-sticking) material and the skin-directed surface of an electrode disc is embedded in the precursor matrix. The system is then exposed to UV light, e.g., of an intensity of 200 Watts per linear inch for a period of less than 30 seconds to polymerize the hydrogel precursor. Preferred compositions, having a ratio of N-vinyl lactam to acrylic monomer of between 9:1 and 1:1, require less than 10 seconds to polymerize. Curing can also occur in situ before the electrode disc is placed in the hydrogel.

A currently preferred electrically conductive precursor composition includes N-vinyl pyrrolidone, acrylic acid, a diacrylate crosslinking agent, 1-hydroxycyclohexyl phenyl ketone as a photoinitiator, potassium chloride, and water. The composition of this invention also is suitable for use as a nonconductive biomedical adhesive in, for example, transdermal drug delivery systems, occlusive bandages, or ostomy gaskets. A preferred composition for such an adhesive contains the following ingredients in the following parts by weight:

| | |
|---|---|
| N-vinyl pyrrolidone | 19.0–35.0 |
| acrylic acid | 4.0–20.0 |
| water | 45.0–65.0 |
| difunctional cross-linking agent | 0.1–1.0 |
| photoinitiator | 0.01–0.2 |

Where conductivity is required, an ionizable salt is included at 0.1–6.0 parts by weight.

BRIEF DESCRIPTION OF THE DRAWING

Like referenced characters in the respective drawn figures indicate corresponding parts.

DETAILED DESCRIPTION

Figure 1:
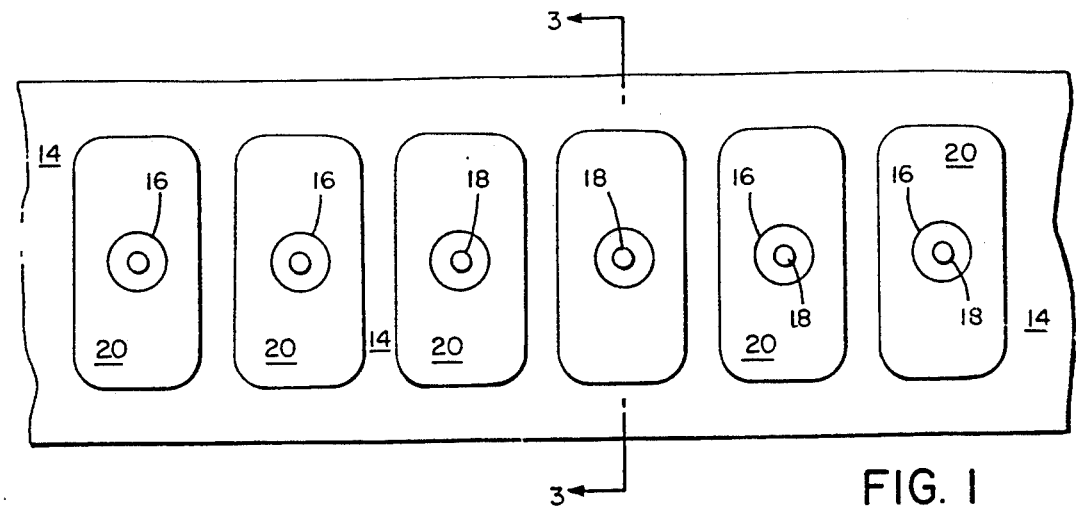
FIG. 1 is a top view of a strip of electrodes of the type which can be fabricated using the process and adhesive of the invention.

The present invention provides electrically conductive hydrogel adhesives comprising a particular ratio of an N-vinyl lactam and acrylic monomer. The compositions also include water, generally in an amount greater than fifty percent by weight. The specific combination of these water-soluble monomers allows the polymerizable precursor to contain a large volume of water that can be absorbed by the finally polymerized and crosslinked matrix, to yield a hydrogel of high electrical conductivity whose tack and cohesion is not compromised by the amount of water absorbed. Moreover, the gel is sufficiently conformable that addition of polyhydric alcohol as a plasticizer or humectant is not required. Finally, the combination of monomers allows the matrix to polymerize very rapidly, thereby simplying manufacturing procedures. For example, embodiments of the hydrogels disclosed herein typically can be cured in less than 30 seconds in the presence of UV light of 200 Watts per inch intensity.

A description of how to make and how to use the composition of the invention is provided below.

A water-soluble, ionizing salt such as a halide, sulfate or citrate salt is first dissolved in water or other aqueous solution. A water-soluble cross-linking agent, and a UV-activatable polymerization initiator (photoinitiator) are then added, followed by the polymerizable monomers. The solution may be heated gently to speed the solubilization of monomers Any one of a number of photoinitiators may be used in the compositions of this invention. A list of useful photoinitiators may be found in the chapter entitled "Photoinitiators" in Adhesive Chemistry (Plenum Publishing, 1984). The currently preferred photoinitiator is 1-hydroxycyclohexyl phenyl ketone sold by Ciba-Geigy under the trade designation, "Irgacure 184".

Similarly, although diacrylates are preferred crosslinking agents in the compositions of this invention, other crosslinking agents may be used. Polyethylene glycol (400) diacrylate is the currently preferred crosslinker. Other suitable crosslinking diacrylates include triethylene glycol diacrylate and tetraethylene glycol diacrylate. The crosslinking agent must be capable of reacting with N-vinyl lactam and acrylic monomers, and therefore must have two or more reactive unsaturated sites.

The preferred monomers are vinyl pyrrolidone and acrylic acid. Other useful N-vinyl lactam monomers include 2-, 3-, and 4-vinyl pyridines. Acrylic acid is highly preferred, but it may be used together with butanediol monoacrylate, polyethylene glycol monoacrylate, propylene glycol monoacrylate, or other acrylic, water soluble monomers.

In accordance with the invention, it has been discovered that the weight ratio of N-vinyl lactam to acrylic monomer has a significant influence on the ability to produce a commercially acceptable hydrogel adhesive having the desired tack, consistency, and rheological properties. Generally, aside from the aqueous salt solution which typically contributes about 60% by weight of the finished adhesive, the mixture of two or more water soluble monomers which include an N-vinyl lactam monomer and an acrylic monomer are the major components of the adhesive, with the photoinitiator and crosslinking agents present in trace quantities typically much less than one percent by weight.

The adhesives of the present invention preferably are formed in situ. i.e., a pre-polymer mixture is prepared as a viscous liquid mixture, deposited at the location where the adhesive is required, then polymerized by exposure to UV light. An example of an electrode for which this adhesive is useful is described below.

Referring now to the drawing, a 0.25 g quantity of the precursor formulation 10 is shown, metered into a cavity 12 formed in a 10 mil thick 14 sheet of styrene or other similarly adhesive, UV-translucent material. The cavity may be, for example, ⅜" by ½" by 1/16" deep. An electrode disc 16 is then embedded in the precursor material. The disc 16 includes a metal snap 18 providing a means of electrically connecting the disc to a lead wire (not shown). The lead wire connecting surface of the snap protrudes through a pad 20, e.g., a 1⅜"×⅜"×1/16" piece of polyethylene foam, or other pliable material, which preferably is coated on its skin-directed surface with a conventional pressure-sensitive adhesive. The dimensions of the pad are sufficient to surround the cavity 12. The pad forms a seal 21 between adhesive material 14 and pad 20 to protect the hydrogel from dehydration during storage. The pad and adhesive provide additional stability when the electrode is separated from the adhesive material 14, affixed to the skin of the patient, and attached to an electrocardiogram or other device.

Figure 2:
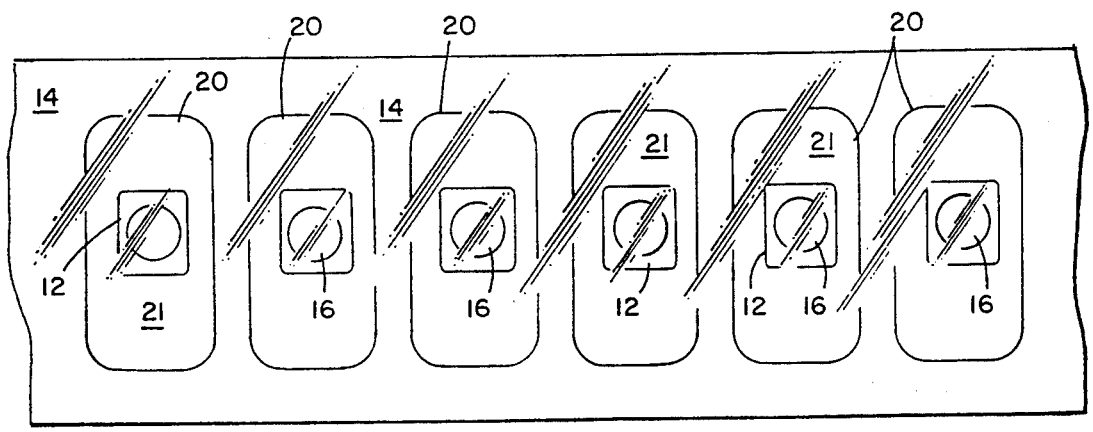
FIG. 2 is a bottom view of the electrode strip of FIG. 1 showing the translucent adhesive backing.
Figure 3:
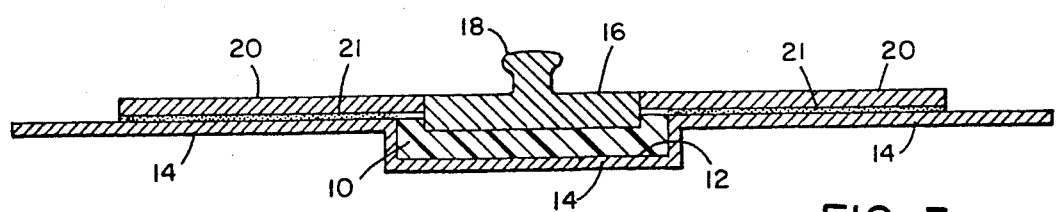
FIG. 3 is a cross-section taken at line 3—3 in FIG. 1 of an electrode comprising the electrically conductive hydrogel adhesive of the invention.

The strip of electrodes is placed with transparent styrene adhesive material 14 facing upward (as illustrated in FIG. 2) and exposed to UV radiation for curing directly through the adhesive 14. For example, the strip may be placed 6" from a UV-irradiator Porticure 1000 lamp, equipped with a 6" long (200 W per linear inch) medium pressure, mercury vapor discharge lamp. Thus, irradiation and curing may be performed in air directly through the styrene sheet (Porticure 1000 is manufactured by American Ultraviolet Engineering, Murray Hill, N.J.). With preferred compositions of the invention, curing is complete in less than 30 seconds exposure under these conditions. Particular formulations require less than a 5 second exposure.

The composition also may be polymerized before placing the electrode disc 16 in the precursor gel 10, in which case the composition may be cured rapidly by direct exposure to the UV light.

Immediately following polymerization, test compositions may be evaluated for initial tack and consistency, using, for example, the procedure described below.

The sample, six inches from a UV-irradiator lamp, is exposed to UV light through the transparent adhesive for five seconds. The hydrogel produced is a soft, tacky hydrogel having a tack rated "D".

EXAMPLES 2-8

In Examples 2-8, the ratio of N-vinyl pyrrolidine to acrylic acid is varied. The constituents of these precursor adhesive compositions, the relative amounts of ingredients, and the initial tack values after curing for various times (2 seconds, 5 seconds, and 30 seconds) are shown in the table below.

TABLE II

| Example Number | 2 | 3 | 4 | 5 | 6 | 7 | 8 |
| --- | --- | --- | --- | --- | --- | --- | --- |
| Potassium chloride | 4.0 | 4.0 | 4.0 | 4.0 | 4.0 | 4.0 | 4.0 |
| Water | 57.84 | 57.84 | 57.84 | 57.84 | 57.84 | 57.84 | 57.84 |
| N-vinyl pyrrolidone | 38.0 | 34.0 | 30.0 | 26.0 | 19.0 | 4.0 | — |
| Acrylic acid | — | 4.0 | 8.0 | 12.0 | 19.0 | 34.0 | 38.0 |
| Irgacure 184 | 0.04 | 0.04 | 0.04 | 0.04 | 0.04 | 0.04 | 0.04 |
| Sartomer 344 | 0.12 | 0.12 | 0.12 | 0.12 | 0.12 | 0.12 | 0.12 |
|  | 100.00 | 100.00 | 100.00 | 100.00 | 100.00 | 100.00 | 100.00 |
| UV Irradiation Time | Initial Tack | | | | | | |
| 2 seconds | A | D | C | C | B | A | A |
| 5 seconds | A | D | D | D | D | C | B |
| 30 seconds | A | F | F | F | F | E | E |

A firm pressure is applied to the sample with the thumb, and the gel is tested for cohesiveness by manual stretching. The samples may be rated qualitatively as follows:
A. Remains a low viscosity liquid.
B. Viscous liquid.
C. Very soft, very leggy, tacky hydrogel.
D. Soft, tacky hydrogel.
E. Firm, tacky hydrogel.
F. Firm, tack-free hydrogel.

The objective is to produce a soft, tacky hydrogel that is not leggy, i.e., one having an initial tack "D". Unpolymerized material, or material grossly undercured, scores "A" or "B". Scores "E" and "F" are too hard to serve as a commercial adhesive, and "F"-rated samples do not have significant adhesive properties. Score "C" produces a composition which can leave a residue on the skin of the patient.

The invention may be further understood from the following non-limiting Examples.

EXAMPLE 1

The currently preferred electrically conductive adhesive of the invention is made by mixing together the following ingredients in the following parts by weight.

TABLE I

| Potassium Chloride | 4.0 |
| --- | --- |
| Water | 57.84 |
| N-vinyl pyrrolidone | 34.0 |
| Acrylic Acid | 4.0 |
| Irgacure 184 | 0.04 |
| Sartomer 344 | 0.12 |

An 0.25 gram quantity of the reaction mixture is placed in the adhesive sheet cavity as illustrated in the drawing, such that the mixture has a thickness of about 0.5 mm. Irgacure 184 is 1-hydroxycyclohexyl phenyl ketone, and may be purchased from Ciba-Geigy. Sartomer 344 is a polyethylene glycol (400) diacrylate crosslinking agent, and may be obtained from Sartomer Corporation.

As can be seen from the foregoing results, adhesive precursor compositions wherein the ratio of N-vinyl lactam to acrylic monomer is between about 10:1 and 1:10 provide hydrogel adhesives of high tack and good conformability. The gels adhere well to the skin surface, yet are sufficiently cohesive to be easily removed without hurting the patient or leaving an undesired residue. In addition, the ionizing salt and large quantity of water in these compositions provides the hydrogels with good electrical conductivity. Moreover, all these compositions polymerize rapidly, in less than 30 seconds exposure to UV light of 200 Watts/inch intensity in air. In fact, vinyl lactam:acrylic monomer ratios of between 9:1 to 1:1 (Examples 3-6) polymerize in less than 10 seconds. Using such compositions one can develop a production curing rate of about 1800 feet/hour, a substantial increase over conventional curing rates.

The foregoing description has been directed to preferred embodiments for the purposes of illustration and explanation. Those skilled in the art will appreciate that many modifications and changes will be possible without departing from the scope and spirit of the invention. The following claims are intended to embrace all such modifications and variations.

What is claimed is:

1. A composition for use in preparing a biomedical adhesive comprising an aqueous mixture consisting essentially of the following ingredients:
   1) water,
   2) a water-soluble cross linking agent,
   3) a photoinitiator,
   4) a monomer component comprising a mixture of an N-vinyl lactam monomer and an acrylic monomer present in a weight ratio greater than about 2:1,
   5) and an ionizable salt the ratio of said ingredients 1-4 being sufficient to result, upon curing in air for less than 30 seconds by exposure to ultraviolet radiation from a lamp of 200 watts per linear inch intensity, in rapid polymerization of said monomers to produce a soft, conformable, essentially dry hydrogel adhesive.

2. The composition of claim 1 characterized in that curing occurs in less than 10 seconds.

3. The composition of claim 1 characterized in that curing occurs in less than 5 seconds.

4. The composition of claim 1 wherein said water-soluble cross-linking agent is a diacrylate.

5. The composition of claim 1 wherein said photoinitiator is 1-hydroxylcyclohexyl phenyl ketone.

6. The composition of claim 1 wherein the acrylic monomer is acrylic acid.

7. The composition of claim 1 wherein the N-vinyl lactam monomer is N-vinyl pyrrolidone.

* * * * *